United States Patent [19]

Arseneault et al.

[11] 4,245,645

[45] Jan. 20, 1981

[54] SELF-LOCKING CEREBRAL ELECTRICAL PROBE

[76] Inventors: Pierre-Michel Arseneault, 7936 de Janville, Charlesbourg, Quebec; Gratien Bouillon, 2571 boul. Wilfrid Laurier, Ste-Foy, Quebec; Roland Picard, 20 Parc Dion, Loretteville, Quebec; Gilles Tremblay, 2015 Helene Boule, Ste-Foy, Quebec, all of Canada

[21] Appl. No.: 926,391

[22] Filed: Jul. 20, 1978

[30] Foreign Application Priority Data

Sep. 28, 1977 [CA] Canada .................................. 287720

[51] Int. Cl.² .............................................. A61B 5/04
[52] U.S. Cl. ..................................... 128/642; 128/731
[58] Field of Search .............. 128/642, 731, 784, 785, 128/786, 303 B

[56] References Cited

U.S. PATENT DOCUMENTS

| | | | |
|---|---|---|---|
| 3,017,887 | 1/1962 | Heyer | 128/303 B X |
| 3,055,370 | 9/1962 | McKinney et al. | 128/303 B |
| 3,089,483 | 5/1963 | Sheetz | 128/642 |
| 3,147,750 | 9/1964 | Fry | 128/642 |
| 3,348,548 | 10/1967 | Chardack | 128/786 |
| 3,825,015 | 7/1974 | Berkovits | 128/786 |

OTHER PUBLICATIONS

IBM Technical Disclosure Bulletin, "Body Tissue Transducer", vol. 6, No. 8, Jan. 1964, pp. 13 & 14.

*Primary Examiner*—Lee S. Cohen
*Attorney, Agent, or Firm*—Schwartz, Jeffery, Schwaab, Mack, Blumenthal & Koch

[57] ABSTRACT

A self-locking encephalic electrical probe is used for stereoelectroencephalographic exploration in the treatment of epilepsy or other brain diseases. The probe includes a long, hollow, flexible tube of small diameter, preferably made of medium density polyethylene. A series of at least two electrically conductive rings, preferably made of silver, are located close to one another along the tube for detecting the electrical activity of nerve cells. A series of insulated electrical conductors are located inside the hollow tube, each conductor connecting a conductive ring to a multi-contact terminal located outside the hollow tube. A removable stylet is inserted into the hollow tube to give it rigidity and to control the direction of introduction of the probe into the brain. The stylet is removed from the tube to restore flexibility to the tube after the probe has been introduced in the brain. A self-locking rigid anchor preferably made of stainless steel holds the probe in place. The anchor is funnel-shaped and quickly and firmly fixes the hollow tube to the brain-pan of the patient after the probe has been introduced to the selected depth in the brain. The probe is used in conjunction with other probes for transmitting to a receptor the cerebral activity of the patient which is recorded and analyzed. As a result of this analysis, a medical staff may accurately locate the region of the brain that must be operated upon to cure the patient.

14 Claims, 10 Drawing Figures

SELF-LOCKING CEREBRAL ELECTRICAL PROBE

BACKGROUND OF THE INVENTION

1. Field of the Invention

The present invention relates to a self-locking cerebral probe for stereolectroencephalographic exploration, and more particularly, to such a probe which may be used to assist in treating epilepsy or other brain diseases.

2. Prior Art and Technical Considerations

Epilepsy is a chronic disease essentially characterized by a more or less frequent repetition of cerebral attacks resulting from a sudden, excessive and anarchic discharge of some nerve cells within the cerebral shell. This frequently results in more or less violent muscular movements of the entire body of the patient and eventually to a sudden fainting spell. Treatment of epilepsy has always caused serious problems for the specialist, essentially due to the difficulty of correctly defining the epileptogen zone and of consequently obtaining the information necessary for selection of the surgical operation to be performed.

Several schools of thought exist on the methodologies that may be used for accurately locating in the cerebral cortex, that is in the grey substance of the brain, the group or groups of abnormal cells which produce electrical discharges in an anarchic manner according to a still unknown mechanism that provokes the crisis of epilepsy.

The specialists of the principal school ground their diagnosis mainly in the study of the intercritical epileptic activity for locating the epileptogen region. This study includes clinical observation, scalp electroencephalography for measuring the electrical activity of the brain, and surface electrocorticography. Surface electrocorticography consists of opening the skull of the patient, depositing on the portion of the exposed brain several recording probes and then electrically stimulating the brain so as to reproduce an epileptic crisis in the patient.

This methodology, which has already been successful for many patients unfortunately has a low yield and a major drawback of confusing the "irritative" zone, which is the zone in which the epileptic activity originates between crises, with the "epileptogen" zone, which is the zone in which the crisis starts. These two zones may coincide but it is presently not known if this is always the case.

Moreover, this methodology is quite "subjective" because the crises of epilepsy are always of short duration and arouse much emotivity in witnesses. Furthermore, the electrical cerebral activity recorded by electroencephalography amounts to only millionths of a volt and is often distorted because it is picked up through the scalp, skull and tuft membranes of the brain.

From this main school, a new school has formed, particularly since publication of the works of Drs. Talairack and Bancaud, M.D., of Paris.

The specialists of this new school also ground their diagnoses on the study of intercritical epileptic activity for locating the epileptogen zone, but they have developed in a more rigorous manner the presently known methodology. The new school does not consider it sufficient to record the spontaneous crisis in order to locate the epileptogen region, to provide a clinical description of the crisis by witnesses and to provide an intercritical recording of several electroencephalograms. The new school has also proposed recording electroencephalograms while simultaneously recording the crisis audiovisually in order to obtain maximum information and to verify, in particular, if the recorded crises fully corresponds to the usual crisis of the patient. Above all, the new school attempts to determine if there is coincidence in time between the electrical discharges of the cells and the clinical manifestations of the disorder. After anatomoclinical correlations have been made and the diagnosis has been set, the epileptogen zone, also known as the "epileptic center", which is the group of cells responsible for the crisis of epilepsy, may be searched.

In order to accomplish this, it is necessary to investigate thoroughly the region of the brain that is involved. This includes the cerebral cortex extending to the surface of the brain, the depths of the lines of the brain, the interhemispheric face, the orbital faces of the frontal lobes and in the deep portion of the temporal lobe. In other words, places not accessible with a surface corticography.

This investigation is performed in the operating room, using a rigid frame also known as a stereotaxical frame, in which the head of the patient is mounted so that all the subsequent steps of the anatomic study may be performed with the same rigorous precision. The frame first enables realization of a neuroradiologic evaluation by teleradiography, including bilateral cerebral angiography, fractionated pneumoencephalography and positive contrast venticulography, in order to precisely determine the positions of the arteries, veins and other structures that are to be investigated. The frame also enables the introduction of as many probes as necessary, generally 8 to 10 probes, in the brain with a very great precision and security, in order to locate the abnormal cells.

The probes permit recording of cerebral activity in depth, which is known as "stereoelectroencephaplographic recording". The electrophysiologic evaluation obtained after having recorded several provoked crisis and several spontaneous crisis with the cervical probes, permits the specialists to precisely define where the epileptogen zone is located and to select the surgical treatment which is appropriate, either with or without opening of the skull.

This new methodology is more "efficient" than the classical methodology since it results presently in cures on the order of 70% of the cases.

However, this new methodlogy as it has been used to date, presents a drawback in that, for several technical reasons, the stereoelectroencephalographic recording can only be carried out under "acute" conditions because of the rigidity of the probes. By acute recording is meant a recording that is made in the operation room in the following manner: the probes are located under general anesthesia; the patient is then awakened and must hold his head fixed in the frame for a period of from 6 to 8 hours so as to record at least one spontaneous crisis or at least one induced crisis.

It is obvious that these recording conditions are not propitious and that the obtained information is worth less than information that could be obtained under more diversified physiological conditions.

OBJECTS OF THE INVENTION

One object of the present invention is to prevent the drawbacks resulting from rigidity of the probes used to date.

Another object of the invention is to provide a cerebral probe for stereoelectroencephalographic exploration, which is flexible and thus enables the specialists to record the cerebral activity of a patient in a continuous manner, that is in a manner where the patient is free to move in a relatively natural manner under constant surveillance of TV cameras, for a period of time which may amount to several weeks, in order to record non-provoked crisis of epilepsy under various and more physiologically natural conditions.

A further object of the invention is to provide a cerebral probe which may be introduced at a desired depth into the brain of a patient with great precision due to a removable stylet which is inserted therein for giving it enough rigidity during its introduction.

A still further object of the invention is to provide a cerebral probe which may be quickly and firmly fixed to the brain-pan of the patient due to an anchor conveniently locked in the bone for avoiding any movement.

SUMMARY OF THE INVENTION

In view of the foregoing objects, the instant invention contemplates a cerebral probe for stereoelectroencephalographic exploration which comprises a long, hollow, flexible tube of small diameter, to be introduced at a given depth in the brain of a patient. A series of at least two electrically conductive rings are located along the tube spaced a small distance from one another for collecting the electrical activity of the nerve cells in the brain. Insulated electrical conductors are located inside the hollow tube and each conductor connects a conductive ring to a terminal located outside the hollow tube. A removable stylet is inserted inside the hollow tube for rigidifying the tube and enabling a directional introduction thereof into the brain. The stylet is removed from the tube to return flexibility to the tube after the probe has been introduced. A self-locking, rigid anchor is provided for quickly and firmly fixing the hollow tube to the brain-pan of the patient after the probe has been inserted to a given depth in the brain.

BRIEF DESCRIPTION OF THE DRAWINGS

Further characteristics and advantages of the invention will be understood with reference to the following description of a non-restrictive embodiment of the invention, taken in connection with the accompanying drawings wherein.

DETAILED DESCRIPTION

Figure 1:
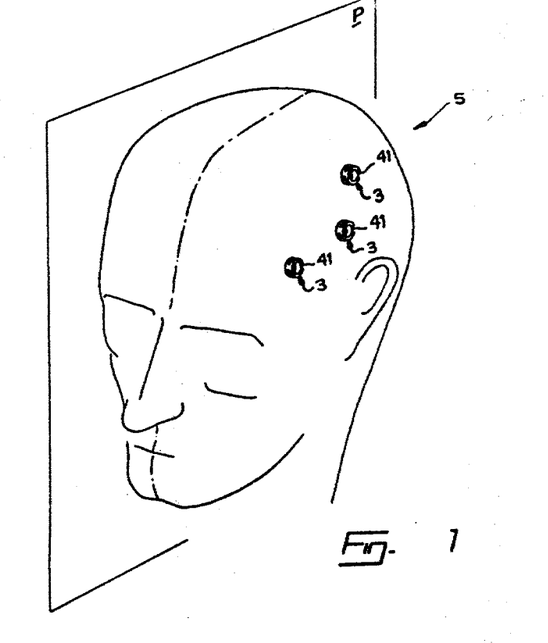
FIG. 1 is a perspective view which represents the head of a patient after introduction of self-locking anchors.
Figure 2:
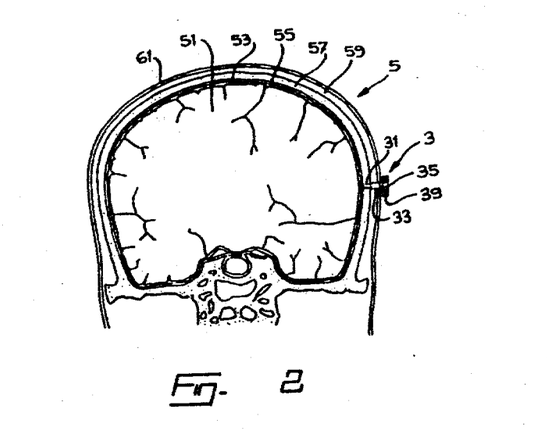
FIG. 2 shows the head of a patient in cross section, after insertion of one self-locking anchor.
Figure 3:
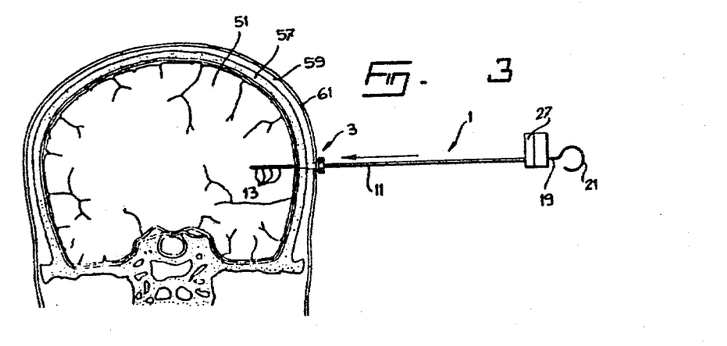
FIG. 3 shows the head of a patient in cross section, during the introduction of a hollow tube of a probe.
Figure 4:
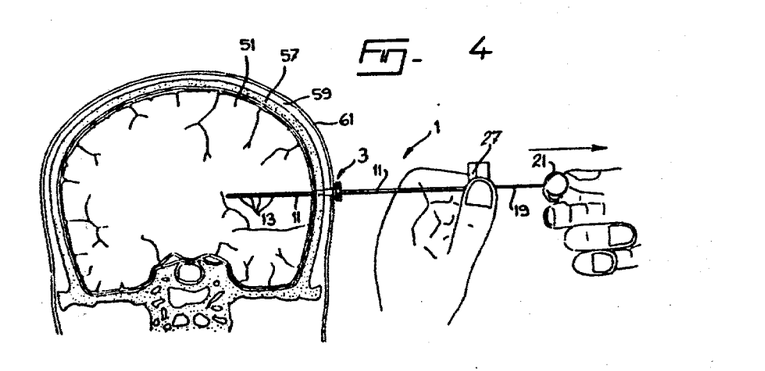
FIG. 4 shows the head of a patient in cross section, when the probe is in position, during removal of a stylet from within the hollow tube.
Figure 5:
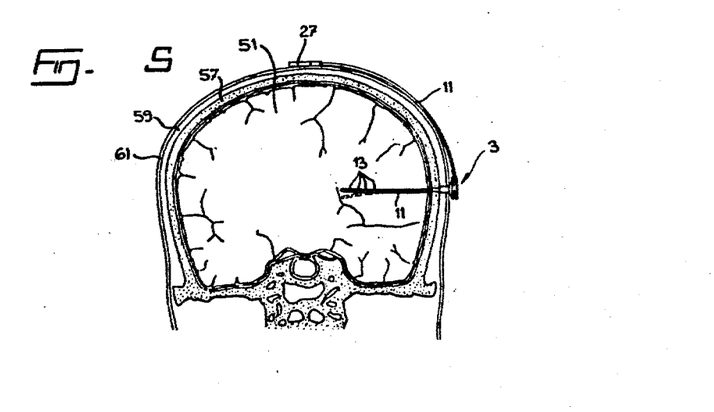
FIG. 5 shows the head of a patient in cross-section, with the probe fixed to a self-locking anchor.
Figures 6, 7:
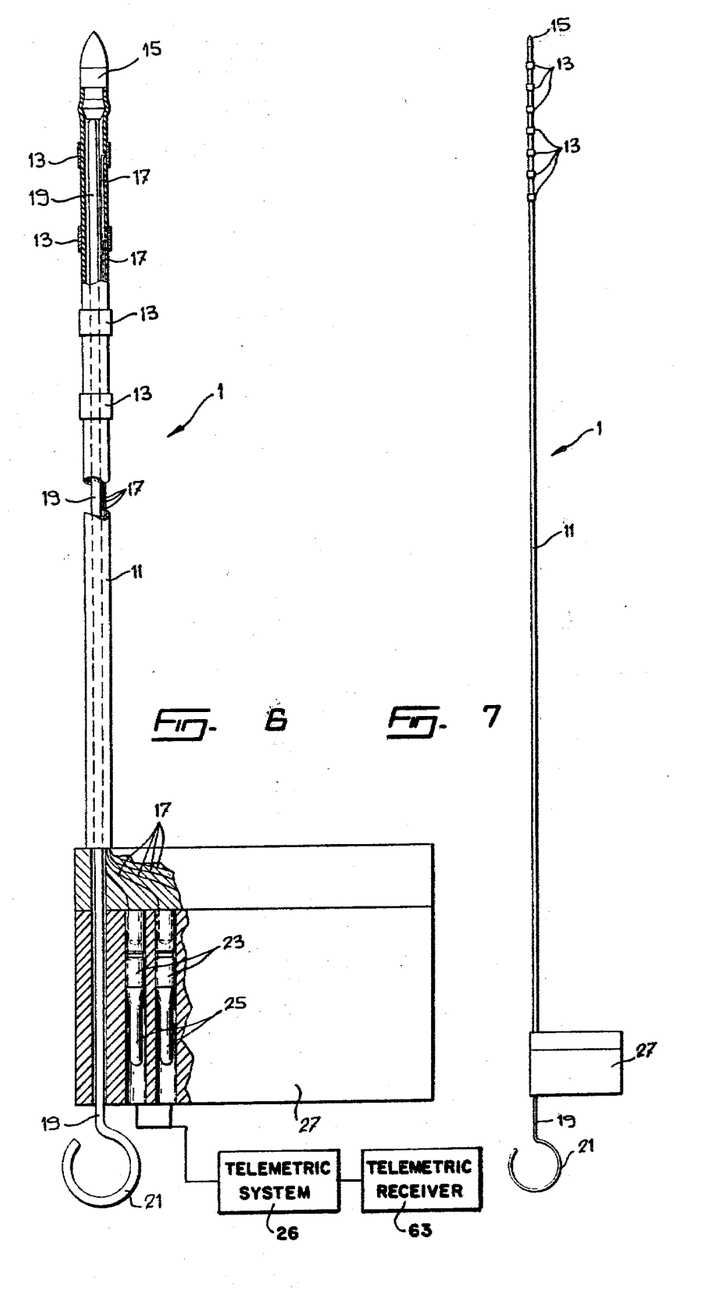
FIG. 6 shows an embodiment of probe according to the invention in partial longitudinal cross section and of an enlarged scale.
FIG. 7 shows the probe of FIG. 6 in a normal scale.

Referring now to FIGS. 6 and 7, it is seen that the cerebral probe 1 for stereoelectroencephalographic exploration comprises: a long, hollow and flexible tube 11 of small diameter; a series of several electrically conductive rings 13, located along the tube 11 at a small distance from each other; a series of insulated electrical conductors 17 located inside the hollow tube, each conductor connecting a conductive ring to a terminal 23 located outside the hollow tube, and a removable stylet 19 inserted inside the hollow tube for giving it rigidity and enabling directional introduction thereof into the brain of a patient.

The hollow tube 11, which is represented at a substantially normal scale on FIG. 7, has a constant diameter of 1.5 mm. Use can be made of tubes having a smaller diameter, insofar as it is technically possible, but it is preferable not to use tubes having a larger diameter so as to prevent any risk of causing brain lesions due to damage or rupture of arteries or veins during introduction of the probe. The hollow tube 11 is made of medium density polyethylene. This material was chosen because of its imperviousness to encephalorachidian liquid and because its texture which renders it acceptable by an organism without occurrence of the rejection phenomenon for a rather long period of time. Furthermore, polyethylene has flexibility which allows the probe, when introduced, to follow the cervical structural movements inside the brain-pan of the patient without risk of injury to the patient.

The thin, electrically conductive rings 13 are located along the tube 11 and fixed to and around the same. The rings 13 are made of silver so as to have a very small electrical impedance and are spaced from each other at a constant interval of about 5 mm from the insertable extremity 15 of the tube. This insertable extremity 15 is also made of silver in order to provide the flexible tube 11 with a rigid tip and thus facilitate the introduction of the probe by giving a solid support to the removable stylet 19. The rigid tip of the insertable extremity 15 is in the shape of a small cap with a nose cone, which is introduced in the hollow extremity of the flexible tube. Of course, the rigid tip can also serve as an electrically conductive element since it is made of silver like the rings 13.

The number of rings disposed along the tube 11 can vary within a range of 2 to 15, including the rigid tip of the insertable extremity 15. The determination of the number of rings to be used of course depends on the number of collecting points that are desired, which number in turn depends on the zone of the brain to be searched. It can be easily understood that the depth at which the probe must be inserted and the surface area to be explored are higher when the probe is inserted for example, in the frontal zone of the brain, than in the temporal lobe of the skull. It can therefore be understood that it is necessary that the probes have a variable number of collecting rings.

The electrically conductive rings 13 as well as the insertable extremity 15 are individually connected to a corresponding number of external terminals 23 by means of a series of insulated electrical conductors 17 passing inside the hollow tube 11. The conductors 17 which are of course very small, are made of silver or copper in order to have a very low electrical impedance.

As aforesaid, each conductor 17 is connected to a conventional terminal 23, such as those manufactured by the Amphenol Company of Chicago, Ill. Each terminal 23 is provided with a contact pin 25 which can be easily connected via a corresponding female plug to a telemetric system 26 attached to the patient, preferably upon his head.

The various terminals 23, the number of which of course depends on the number of conductive rings, are located side by side at small intervals from one another in a small plate 27 made of extruded, insulated plastic material, so as to be perfectly insulated from one another while forming a compact unit. The small plate 27 is fixed to the "free" extremity of the probe 1, that is the extremity which extends outwards the brain of the patient, as an extension of the hollow tube 11, forming an integral unit therewith.

The removable stylet 19 is used for facilitating the introduction of the probe 1 in the brain of the patient by giving the hollow tube 11 some rigidity, thereby providing precision during the introduction of the probe. The stylet 19 consists of a small wire made of stainless steel, having a diameter selected to allow it to slide easily inside the hollow tube 11 without damaging the conductors 17, while ensuring enough rigidity to the probe 1. The stylet 19 has a loop 21 formed at its free end which is easy to seize for facilitating its extraction from the hollow tube 11 when the probe has been inserted in the brain.

Figures 8, 9:
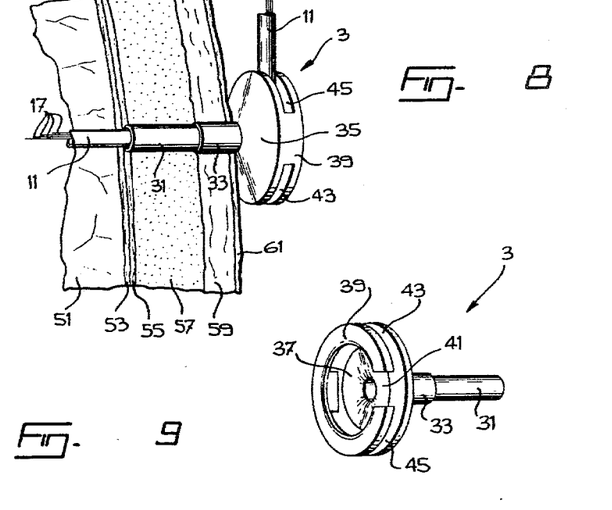
FIG. 8 is a perspective view partially in section and showing a preferred embodiment of the self-locking anchor in position in a bone.
FIG. 9 shows the anchor of FIG. 8 in perspective and from the other end.

Referring now to FIGS. 8 and 9, each cerebral probe 1 after having been introduced in the brain, is fixed and solidly held to the brain-pan of the patient by means of a rigid anchor 3 made of stainless steel. The anchor 3 which is in the shape of a small funnel, comprises four sections coaxially disposed and respectively numbered 31, 33, 35 and 39.

The first section 31 is inserted in a bone 57 of the head 5 of the patient up to the internal tabula 55 thereof. This first section 31, which is hollow and cylindrical so as to provide an opening for and to guide the probe 1 during its introduction in the brain 51 of the patient, is of variable length, for the same reasons as previously indicated in connection with the dimension of and the number of rings on the probes; i.e. the length of the section 31 obviously depends on the thickness of the bone in which it has to be inserted.

The second section 33 is inserted in the muscle 59 which covers the bone 57 of the skull. This second section 33 which is also hollow and cylindrical so as to provide an opening for and to guide the probe 1 during its introduction, has a diameter slightly larger than that of the first section 31 so as to bear against the bone for a better fixation of the anchor to the head of the patient. In addition, the larger diameter of section 33 helps reinforce the connection of the first section 31 to the third conical section 35 and above all, as will be described hereinafter, allows the countersinking of a curved bore 37 inside the anchor to provide the hollow tube 11 with better seating so as to avoid breaking the hollow tube during its fixation. The second section 33, of course, has a variable length depending on the thickness of the muscle that it has to penetrate.

The third section 35 is used for relieving the skin 61 which covers the muscle 59. The third section is a truncated hollow cone with a vertex of about 135°, which has a curved and very flared internal surface 37 forming a funnel. The external shape of the third section 35 has large diameter cross section which is much larger than the diameter of the second section 33, and is intended not only for avoiding an accidental and unfortunate penetration of the anchor 3 into the skull during the treatment, which could be very dangerous for the patient, but also for avoiding, because of its truncated shape, excessive contact of the anchor with the skin, which could provoke allergies or any other trouble generally encountered when an extraneous body contacts human skin. The internal surface 37 of the third section 35 which is inwardly curved and very flared, provides the probe and more particularly the hollow tube 11 with the best possible seating during its introduction into the brain and its fixation thereto, thereby avoiding any eventual breaking or tearing of the hollow tube 11 due to engagement with a sharp edge.

The fourth and last section 39 of the anchor 3 is specifically used for solidly fixing the hollow tube when it has been introduced in the brain at a desired depth. This fourth section 39 is hollow and of cylindrical shape and has the same diameter as that of the great circle of the third section that extends coaxially therewith. The fourth section 39 is provided with a wide longitudinal slot 41 parallel to the axis of the cylinder, which extends over substantially the entire length thereof from the free end of the anchor. The fourth section 39 is also provided with two small lateral slots 43 and 45 which extend in directions perpendicular to the longitudinal slot 41 symmetrically from each side thereof, in the middle of the cylinder over substantially the entire periphery thereof. The two small slots 43 and 45 are of the same width and are slightly smaller than the diameter of the hollow tube 11 so that the latter may be strongly wedged therein thereby solidly holding the probe at the desired depth in the brain of the patient. For this purpose, the two small slots 43 and 45 are each provided with a small round shaped recess (not shown), radially oriented with respect to the cylinder and located at right angle with respect to the plane passing through the large slot 41 on one side or the other of the latter. This recess (not shown) enables the hollow tube 11 to be "centered" in the small lateral slots 43 and 45 when the probe 1 is fixed.

The utilization, insertion and operation of the above described cerebral probe 1 will be now described with reference to FIGS. 1 to 5 and FIG. 10.

In accordance with the methodology of practicing the instant invention, at least three spontaneous crises of the patient are first recorded by electroencephalography and visually and audibly by a TV set or the like, in order to confirm if the recorded crises effectively corresponds to the usual crises of the patient. When this first observation is completed and the diagnoses is settled regarding the zone of the brain to be cured, then an anatomical investigation is effected.

For this purpose, use is made of a stereotaxial frame that is centered with respect to the head of the patient so that the anatomical median line of the patient be parallel to the instrumental line of the frame. Stereoscopic radiographies are taken so as to obtain a three dimensional view of the cerebral structures. Since the coordinates in height with respect to the diagram are constant, the radiographs of the face of the patient can be easily associated to the radiographs of the profile thereof so as to precisely locate the position of the different parts of the brain in space with respect to the frame.

These stereoscopic radiographs are performed in order to locate the arteries of the brain by coloration (bilateral cerebral arteriography) and to visualize the subarachnoidian spaces and the ventricular system by introduction of air or other contrasting products (fractioned pneumoencephalography and positive contrast-ventriculography).

This anatomical investigation is very important since it permits one to locate the position of the arteries, the veins and the various structures or cortical surfaces that must be examined and thus helps plan the subsequent operation which is the insertion of cerebral probes 1 in order to obtain a complementary "electrophysiological" evaluation.

The insertion of the cerebral probes 1 is carried out in a very precise manner by using the stereotaxical frame for supporting the surgical instruments and, as aforesaid, as a spatial reference.

First of all, the skin 61 and the muscle 59 are bored with a drill having a small diameter of about 2.4 mm. After contact with the external portion of the bone, the drilling is continued up to encountering the compact osseous tissue of the internal portion of the skull, usually called internal tabula 55. Generally, the boring is carried out in a direction perpendicular to the anatomic median plane of the patient, that is perpendicularly to the plane P (see FIG. 1) passing through the bridge of the nose and between the eyes of the patient.

The choice of this direction is determined by the method of introducing the probes 1 stiffened by the stylet 19 along a rectilinear direction inside the brain. The diverse points where the probes 1 are introduced, are selected by the specialists so as to enable the probes to follow a linear movement in the brain without risk of damaging arteries or veins. The paths are selected according to the results of the preliminary evaluation of the radiographies which, as aforesaid, have been taken according to a facial or profile directions.

When the bone 57 has been bored, the layers of tough membrane 53 surrounding the brain are burned with a small metallic pin. After the membranes have been coagulated by the heat, a metallic anchor 3 is introduced in the hole. The respective lengths of the first and second sections of the anchor 3 are selected with respect to the thicknesses of the traversed layers of muscles and bone. The end surface of the fourth section 39 is located in a plane parallel to the plane P (see FIGS. 1 and 2). Each anchor 3 is disposed in the skull so that its wide longitudinal slot 41 is oriented to open in a horizontal plane with respect to the head 5 of the patient in order to subsequently solidly fix the hollow tube 11 by wedging in the small slots 43 or 45 in a vertical direction and so as to group all of the terminals 23 or multi-contact terminals 27 on the top of the patient's head (see FIG. 10).

When an anchor 3 has been inserted and is sufficiently held by the bone to avoid any possible movement, a probe 1 is introduced in the brain 51. The probe 1 is gradually inserted to the desired depth. Due to the relative rigidity of stylet 19 one is able to achieve excellent precision regarding the selected direction perpendicular to the plane P (see FIG. 3).

When the probe 1 is introduced to the desired depth, the stylet 19 is removed (see FIG. 4) and the hollow tube 11 is fixed to the anchor 3 by bending the end of the tube and inserting the tube first through the slot 41 and then through either slot 43 or the slot 45 up to the recess (not shown). Since the probe 1 is flexible (see FIG. 5) and therefore able to "follow", without risk of lesions, the continual movements of the brain inside the brain-pan, the patient can be awaked and can live under relatively good physiological conditions during his examination which may last about three weeks. With the probe 1 implanted the patient can move and even walk.

Figure 10:
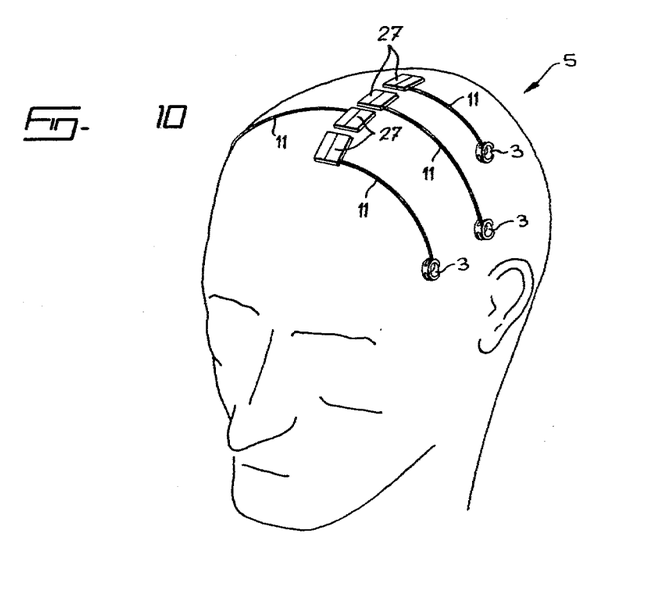
FIG. 10 shows in perspective the head of a patient after the insertion of self-locking anchors and the introduction and fixation of the probes.

When all the probes are introduced, the various connectors 27 are grouped onto the top of the head 5 of the patient, where they are connected to a telemetric system of the PAM-FM type. This telemetric system can either be wireless or connected by wires and must be of a small size so as to be easily attached to the head of the patient.

The telemetric system transmits on a FM channel, or by means of a wire, the various information collected by the probes. This information includes the durations and intensities of electrical discharges emitted by the cells of the brain. The transmitted information is received by a receiver 63 where it is decoded and recorded by means of a graphic recorder. This recording is carried out simultaneously with other visual and sound recordings performed by a camera, a microphone and a magnetoscope to the correlation between the various apparent symptoms and the recorded information for every crisis.

Usually, three spontaneous crisis are recorded. Several crises provoked by an electrical stimulation are also recorded. To provoke such crises, use can be made of the probes 1 which serve not only for recording electrical discharges from the cells, but also to transmit to the brain electrical impulses programmed by the specialists, according to the information that they want to verify.

The following various types of information exemplify information which can be obtained by using cerebral probes according to the invention:

localization and intensity of low activity during the inter-critical recordings:

localization and intensity of inter-critical irritative activity;

localization of the zone from which the critical (tonic or convulsive) activity starts and the speed at which the same reaches the surrounding probes;

duration and intensity of the critical (tonic or convulsive) activity at each ring of each probe;

intensity and duration of post-critical exhausting;

correlations in time between the electrical activity at the rings and clinical manifestations;

value of electric stimulation necessary for obtaining a local post-discharge; and diffusion, intensity and duration of the post-discharge after a predetermined stimulation.

The information recorded during the spontaneous and provoked crises is analyzed to determine the general parameters already discussed in the BACKGROUND OF THE INVENTION, which parameters enable the specialists to determine the epiloptogen zone with precision. The patient then can be operated by the surgeons who know exactly where and how to proceed.

What is claimed is:

1. A probe for electroencephalographic exploration of a patient's brain after being secured to the patient's brain-pan, comprising:

a flexible tube of small diameter for insertion to a given depth in the brain of a patient;

at least two electrically conductive rings spaced along the flexible tube at relatively small distances from one another for detecting electrical activity of nerve cells in the brain;

a terminal block located outside the tube and having a plurality of terminals;

a plurality of insulated electrical conductors located inside the flexible tube, each conductor connecting one of the conductive rings to one of the terminals of the terminal block;

a removable stylet inserted inside the flexible tube for giving rigidity to the flexible tube and for enabling a directional insertion thereof into the brain whereby when the stylet is removed from the flexible tube after the tube has been inserted into the brain flexibility returns to the tube, the flexible tube and stylet each having one end for insertion into the patient's brain and a free end opposite the one end; and a self-locking, rigid anchor, the anchor including means for securing the anchor with respect to the brain-pan and means for quickly and firmly fixing the flexible tube to said anchor after the tube has been inserted to a given depth in the brain.

2. A probe as claimed in claim 1, wherein:

the flexible tube is made of medium density polyethylene and has an external diameter of substantially almost 1.5 mm;

the conductive rings are made of silver and comprise from five to ten elements spaced from each other at a constant interval of about 5 mm from the one end of the tube;

the removable stylet is made of stainless steel and is provided at its free end with a loop which is easy to seize so as to facilitate extraction of the one end of the stylet from the flexible tube when the probe has been introduced in the brain; and the anchor is made of stainless steel and is in the shape of a small funnel through which the flexible tube is introduced.

3. The probe as claimed in claim 2, wherein the anchor comprises:

a first hollow section of cylindrical shape for insertion through the bone of the skull of the patient to the level of the internal tabula of the brain in order to provide an opening for the flexible tube and in order to guide the flexible tube;

a second hollow cylindrical section coaxial with and connected to the first section and having a diameter slightly larger than the diameter of the first section, the second section being for insertion through the muscle which covers the skull to provide an opening for the flexible tube;

a third section, coaxial with and connected to the second section wherein the third section is a hollow truncated cone having a curved and flared internal surface, the third section being for bearing against the skin of the patient and permitting the relatively easy introduction of the flexible tube into the first and second sections and subsequently into the brain; and a fourth section of cylindrical shape attached to the third conical section, wherein the fourth section includes a lateral slot extending and opening longitudinally and two other slots registered with the lateral slot and extending partially around the fourth section, the slots selectively receiving and wedging the flexible tube in place once the stylet has been removed.

4. The probe as claimed in claim 3, wherein the terminals to which the conductors are connected are located outside of the flexible tube and are arranged side by side within the terminal block and wherein the terminal block is fixed to the free end of the tube so as to form a unit therewith.

5. The probe as claimed in claim 1, wherein the terminals to which the conductors are connected are located outside of the flexible tube and are arranged side by side within the terminal block and wherein the terminal block is fixed to the free end of the tube so as to form a unit therewith.

6. The probe as claimed in claim 1 further including a conductive tip disposed at the one end of the flexible tube, the conductive tip being connected to one of the electrical conductors.

7. A system for conducting an electroencephalographic exploration of a patient's brain comprising a telemetric system, a telemetric receiver, and a probe coupled with said telemetric system so that information detected by the probe is transmitted by the telemetric system to the telemetric receiver, the telemetric receiver including means for decoding and recoding the transmitted information, the probe being for insertion into a patient's brain and being for attachment to the patient's brain-pan, the probe comprising:

a flexible tube of small diameter for insertion to a given depth in the brain of a patient;

at least two electrically conductive rings spaced along the flexible tube at relatively small distances from one another for detecting electrical activity of nerve cells in the brain;

a terminal block located outside the tube and having a plurality of terminals;

a plurality of insulated electrical conductors located inside the flexible tube, each conductor connecting one of the conductive rings to one of the terminals of the terminal block, the telemetric system being connected to the terminal block;

a removable stylet inserted inside the flexible tube for giving rigidity to the flexible tube and for enabling a directional insertion thereof into the brain, whereby, when the stylet is removed from the flexible tube after the tube has been inserted into the brain, flexibility returns to the tube; and a self-locking, rigid anchor, the anchor including means for securing the anchor with respect to the brain pan and means for quickly and firmly fixing the flexible tube to said anchor after the tube has been inserted to a given depth in the brain.

8. A method of conducting an electroencephalographic exploration of a patient's brain comprising the steps of:

(a) boring a hole through the patient's scalp, scalp muscle and skull to the level of the tubula of the brain;

(b) inserting a hollow guide through the hole and anchoring the guide to the skull;

(c) inserting a flexible probe stiffened by a rigid stylet through the internal tubula and into the brain, said flexible probe being electrically sensitive through the hollow guide;

(d) restoring flexibility to the probe by withdrawing the rigid stylet from the probe;

(e) securing the probe to the guide; and (f) monitoring electrical activity within the brain by detecting electrical signals with the probe.

9. The method of claim 8 further including the steps of:

repeating steps (a) through (f) at a plurality of locations on the patient's head to obtain signals from various locations within the patient's brain.

10. The method of claim 9 wherein step (f) includes detecting signals at different positions along the length of the probe to determine the depth within the brain at which the signals occur.

11. The method of claim 8 or 9 further including the step of:

obtaining stereoscopic radiographics of the patient's brain prior to boring the holes to locate arteries and veins so that the arteries and veins may be avoided when inserting a probe.

12. The method of claim 8 wherein in step (f) monitoring is accomplished by transmitting radio signals from a transmitter connected to the probe and secured to the patient's head at a location spaced from a remotely located receiver.

13. The method of claim 8 further including the step of monitoring the patient audio-visually while performing step (f) in order to correlate electrical brain activity with physiological behavior.

14. The method of claim 8 further including the step of inducing electrical activity in the brain by supplying electrical current to the probe from a source external to the brain.

* * * * *